US012386936B2

(12) United States Patent
Lock

(10) Patent No.: US 12,386,936 B2
(45) Date of Patent: *Aug. 12, 2025

(54) BIOMETRIC IDENTIFICATION AND CONTROL SYSTEMS AND METHODS FOR PROVIDING CUSTOMIZABLE SECURITY THROUGH AUTHENTICATION OF BIOSIGNAL REPRESENTATIONS OF ONE OR MORE USER-SPECIFIC AND USER-SELECTED GESTURE-INTENTIONS

(71) Applicant: HARLOCK CREATIVE LLC, Chicago, IL (US)

(72) Inventor: Blair Andrew Lock, Wilmette, IL (US)

(73) Assignee: HARLOCK CREATIVE LLC, Chicago, IL (US)

( * ) Notice: Subject to any disclaimer, the term of this patent is extended or adjusted under 35 U.S.C. 154(b) by 26 days.

This patent is subject to a terminal disclaimer.

(21) Appl. No.: 18/538,030

(22) Filed: Dec. 13, 2023

(65) Prior Publication Data
US 2024/0111851 A1 Apr. 4, 2024

Related U.S. Application Data

(63) Continuation of application No. 17/007,431, filed on Aug. 31, 2020, now Pat. No. 11,886,559.

(51) Int. Cl.
*G06F 21/32* (2013.01)
*G06N 20/00* (2019.01)

(52) U.S. Cl.
CPC ............. *G06F 21/32* (2013.01); *G06N 20/00* (2019.01)

(58) Field of Classification Search
CPC .......... G06F 21/32; G06F 3/015; G06F 3/017; G06N 20/00; G06N 3/045; G06N 5/01;
(Continued)

(56) References Cited

U.S. PATENT DOCUMENTS 8,812,096 B2   8/2014   Flaherty et al.
9,883,815 B2   2/2018   Einarsson et al.
(Continued)

FOREIGN PATENT DOCUMENTS

CA   3029445 A1    1/2018
DE   69630713 T2  12/2004
(Continued)

OTHER PUBLICATIONS

Arduino based hand gesture control of your computer, Electronics Hub, downloaded from the Internet at: <https://www.electronicshub.org/arduino-based-hand-gesture-control-computer/> (Nov. 15, 2017).
(Continued)

*Primary Examiner* — Towfiq Elahi
(74) *Attorney, Agent, or Firm* — MARSHALL, GERSTEIN & BORUN LLP

(57) ABSTRACT

In various aspects, systems and methods are described for a biometric identification and control for providing customizable security through authentication of biosignal representations and control. The biometric identification and control systems and methods comprise hardware and software components that are used to detect, via a biometric detection device, biometric signals of a user. These biosignals are analyzed by a processor communicatively coupled to the biometric detection device. After analyzation of the biosignals, a biometric profile is created and used with a security interface to access a secure resource or device or to output a command to another device.

24 Claims, 7 Drawing Sheets

(58) Field of Classification Search
CPC ........ G06N 20/10; G06N 20/20; A61B 5/117; H04L 63/0861
See application file for complete search history.

(56) References Cited

U.S. PATENT DOCUMENTS

| | | |
|---|---|---|
| 10,124,484 B1 | 11/2018 | Barnes |
| 10,437,335 B2 | 10/2019 | Daniels |
| 2014/0063055 A1 | 3/2014 | Osterhout et al. |
| 2015/0074797 A1* | 3/2015 | Choi ................ H04W 12/065 726/19 |
| 2016/0324677 A1 | 11/2016 | Hyde et al. |
| 2017/0123487 A1 | 5/2017 | Hazra et al. |
| 2017/0193314 A1 | 7/2017 | Kim et al. |
| 2018/0012009 A1* | 1/2018 | Furman ................ G06N 3/088 |
| 2019/0384901 A1 | 12/2019 | Osborn et al. |
| 2020/0042089 A1 | 2/2020 | Ang et al. |
| 2020/0065569 A1 | 2/2020 | Nduka et al. |
| 2020/0233452 A1 | 7/2020 | von Badinski et al. |

FOREIGN PATENT DOCUMENTS

| | | |
|---|---|---|
| DE | 102015210638 A1 | 12/2016 |
| EP | 3368966 A1 | 9/2018 |
| JP | 2019524204 A | 9/2019 |
| KR | 20190083611 A | 7/2019 |

OTHER PUBLICATIONS

Geng et al., Gesture recognition by instantaneous surface EMG images, Sci. Rep., 6, Article No. 36571 (2016).

International Application No. PCT/US21/26952, International Search Report and Written Opinion, mailed Jul. 16, 2021.

Jaber et al., Robust hand gesture identification using envelope of HD-sEMG signal, ICICT '19: Proceedings of the International Conference on Information and Communication Technolog, pp. 203-209 (2019).

Naik et al., Subtle hand gesture identification for HCI using temporal decorrelation source seperation BSS of surface EMG, 9th Biennial Conference of the Australian Pattern Recognition Society on Digital Image Computing Techniques and Applications (DICTA 2007) (2007).

Roberts et al., Interpreting muscle function from EMG: lessons learned from direct measurements of muscle force, Integr. Comp. Biol., 48(2):312-20 (2008).

European Application No. 21862254.6, Extended European Search Report, dated Aug. 22, 2024.

* cited by examiner

BIOMETRIC IDENTIFICATION AND CONTROL SYSTEMS AND METHODS FOR PROVIDING CUSTOMIZABLE SECURITY THROUGH AUTHENTICATION OF BIOSIGNAL REPRESENTATIONS OF ONE OR MORE USER-SPECIFIC AND USER-SELECTED GESTURE-INTENTIONS

RELATED APPLICATION(S)

This application claims the benefit of U.S. application Ser. No. 17/007,431 (filed on Aug. 31, 2020), the entirety of which is incorporated by reference herein.

FIELD OF THE DISCLOSURE

The present disclosure generally relates to biometric security, and, more particularly to biometric identification and control systems and methods for providing customizable security through authentication of biosignal representations of one or more user-specific and user-selected gesture-intentions.

BACKGROUND

As technology becomes more integrated into our everyday lives, the importance for security becomes greater. Traditional methods of password protection are slowly becoming antiquated due to new biometric scanners, such as seen on cellphones as thumbprint scanners. Current widely used forms of security authentication lack high level security. Passwords and codes can be hacked, guessed, or forgotten, and can be time intensive to enter. In addition, conventional methods for security to unlock physical objects, such as a door, typically involve using a lock and key. However, this method has drawbacks. For example, a key must always be carried. This causes the potential for keys to be lost, stolen, or copied.

For the foregoing reasons, there is a need for enhanced security that can be administered by an authenticated user only. More specifically, there is a need for biometric identification and control systems and methods for providing customizable security through authentication of biosignal representations of one or more user-specific and user-selected gesture-intentions, as described herein.

BRIEF SUMMARY

The disclosed invention herein eliminates these problems through novel systems and methods of authentication and security protection. The disclosure herein describes biometric identification and control systems and methods that use voluntary biometric signals of a user for authentication, providing a low, if not impossible, likelihood of the user's unique biometric signals being replicated. For example, it would be difficult, if not impossible, for hacker or thief to recreate the specific biometric signals of a particular user, even if the hacker or thief knew a given user-specific and user-selected gesture-intention of a user as described herein. In comparison, keys (e.g., hardware keys or computer security keys) can be copied or stolen, and locks can be picked or hacked, all of which demonstrate a vulnerable and lower level of security.

Personal security, as described herein, and which is unique and specific to a given user, can be accomplished using voluntary biometric signals. For example, every tissue in the body is electrically active, creating small levels of electricity when used or even when idle. Much like a fingerprint, these levels of electricity are completely unique to each user. These patterns of signals can take many different forms and be measured through various means, such as electromyography, electrocardiography, infrared, ultrasound, photodiodes, accelerometers, and gyroscopes. These biometric signals also differ if a user performs a specific motion. For example, making a first or doing a "thumbs-up" motion or gesture, and/or an "okay" motion or gesture, would create different biometric signals, which would be unique to the user. If a first user were to perform the exact same motion as a second user, then the first user would produce a different pattern of biometric signals than the second user. The unique biometric signal patterns can be used for security authentication and executing commands, especially when used in combination of voluntary signals that can only be created by an authenticated user. The user will be able to execute these commands simply by performing a voluntary action, recreating their unique set of voluntary biometric signals, thereby enabling biometric authentication based on not only their unique gestures, but also their unique biometric signals creates by those unique gestures. Additionally, or alternatively, voluntary actions may also be performed in sequence for more advanced security measures, such as: making a fist, followed by a thumbs up, followed by a wave, etc.

Accordingly, a need for the invention arises from the necessity of requiring a technology that allows rapid security authentication and execution of commands in relation to voluntary biometric signals that are uniquely generated by a user. These biometric signals are specific to a single user (based on his or her own generated biometric signals by his or her muscles or groups of muscles), which therefore can be used to provide a unique and high level of security on a per-user basis.

A need for the invention also arises from the necessity of requiring a technology that allows for enhanced personal security, and through the necessity of requiring a single technology that can conduct biometric authentication for one or many secure resources or devices, as described herein.

Various embodiments of the present disclosure are described herein regarding identifying and/or categorizing voluntary movement biometric signals to provide security based on biometric signals. Such embodiments may include collecting and analyzing voluntarily-generated biometric data, using the analyzed data to authenticate the user and/or execute software and hardware commands, and/or creating biometric profiles and customizable commands to facilitate enhanced security. A need for embodiments of the of the present disclosure arises from the necessity of having a method to rapidly detect biometric signals from a user and categorize signals as voluntary, and upon subsequent comparison with a second set of biometric data, performing a security operation as predetermined by the user. The embodiments as described herein describe biometric systems and methods that allow a user to quickly categorize voluntary movements for controlling access to secure resource(s) or device(s), which can include third party devices. In one or more embodiments, during a given data collection session, the collection of biometric data from the user may guide a user through the process of generating voluntary biometric data. The system may then provide feedback on the data collected, before storing the data as a first set of biometric data for a voluntary motion for that user. In various embodiments, when the user conducts a voluntary motion, the system and methods describe herein may receive voluntary motion data and compare it to the first set of voluntary biometric data, upon substantial similarity between data sets, performing a security authentication program that may be coupled to a secure resource or device, such as a third party device or program.

In still further embodiments, a biometric identification and control system is described. The biometric identification and control system is configured to provide customizable security through authentication of biosignal representations of one or more user-specific and user-selected gesture-intentions. The biometric identification and control system comprises a biometric detection device configured to detect biometric signal data of a user. The biometric identification and control system further comprises a processor communicatively coupled to the biometric detection device. The biometric identification and control system further comprises a biometric software component comprising computing instructions executable by the processor. Execution of the computing instructions by the processor causes the processor to perform an analysis of the biometric signal data of the user as detected by the biometric detection device. In addition, execution of the computing instructions by the processor causes the processor to create a biometric profile based on the analysis of the biometric signal data. In various embodiments, the biometric profile comprises an electronic recording of a biosignal representation of a user-specific and user-selected gesture-intention of the user. In addition, execution of the computing instructions by the processor causes the processor to bind the user-specific and user-selected gesture-intention of the user to a security interface. The security interface is operable to provide authentication of the user for access to a secure resource or device.

In additional embodiments, a biometric identification and control method is described regarding providing customizable security through authentication of biosignal representations of one or more user-specific and user-selected gesture-intentions. The biometric identification and control method comprises performing, by a biometric software component executed by a processor communicatively coupled to a biometric detection device, an analysis of biometric signal data of a user as detected by the biometric detection device. The biometric identification and control method further comprises creating, by the biometric software component, a biometric profile based on the analysis of the biometric signal data. The biometric profile comprises an electronic recording of a biosignal representation of a user-specific and user-selected gesture-intention of the user. The biometric identification and control method further comprises binding, by the biometric software component, the user-specific and user-selected gesture-intention of the user to a security interface. The security interface is operable to provide authentication of the user for access to a secure resource or device.

In still further embodiments, a tangible, non-transitory computer-readable medium stores instructions for providing customizable security through authentication of biosignal representations of one or more user-specific and user-selected gesture-intentions. The instructions, when executed by one or more processors, cause the one or more processors to perform, by a biometric software component executed by a processor communicatively coupled to a biometric detection device, an analysis of biometric signal data of a user as detected by the biometric detection device. The instructions, when executed by one or more processors, further cause the one or more processors to create, by the biometric software component, a biometric profile based on the analysis of the biometric signal data. The biometric profile comprises an electronic recording of a biosignal representation of a user-specific and user-selected gesture-intention of the user. The instructions, when executed by one or more processors, further cause the one or more processors to bind, by the biometric software component, the user-specific and user-selected gesture-intention of the user to a security interface. The security interface is operable to provide authentication of the user for access to a secure resource or device.

The representative embodiments of the present invention provide numerous advantages over commonly used methods for providing biometric security and detection of biometric signals. The general purpose of the invention is to provide a method for highly secure, accurate, yet simple and quick, biometric authentication for a user that may be completed through the voluntary generation of biometric signals. In various embodiments, the many novel features described result in a new method for determining the identify of a user and authenticating the use of a secure resource or device (e.g., a third party device) through a successful match or otherwise detection of voluntary biometric data as generated by the user.

In various embodiments, a user may perform a gesture or gesture intention and the system may then detect and analyze the biometric signals produced. Additionally, or alternatively, the systems and/or methods described herein may store, e.g., in a memory, the biometric signals and/or pattern of signals as a key or otherwise an authentication key. The systems and/or methods may then analyze the user's biometric signals for a second pattern of signals. If the second analyzed pattern is the same as the first analyzed pattern, then the system may authenticate the user and perform the intended command. This can be hardware or software command and both the gesture/gesture-intention and the command output can be customizable. If a second analyzed pattern is not the same as the first analyzed pattern, then the device does not authenticate the user and the user will not be able to access the system or execute the intended command.

As described herein, the present invention generally comprises a biometric collection and authentication system configured to provide customizable security through comparison of biometric signal representations of one or more user-specific and user-selected gesture-intentions. The biometric signals are identified by a biometric detection device. A processor is communicatively coupled to the biometric detection device and performs and analysis of the biometric signal data of the user and executes computing instructions. These computing instructions cause the device to perform an analysis of the biometric signal data detected form the user, and create a biometric profile based on the biometric signal data related to a user's voluntary gesture or gesture intention. The biometric profile is used to provide authentication of the user for access to a secure resource or device or to communicate computer commands to another device.

This biometric and identification control system may further comprise a user interface that allows the user to customize the security interface in accordance with the user's selected voluntary gesture or selected gesture-intentions. This user interface can be comprised of a tactile based, auditory, or a virtual based user interface. The user interface is used to create customized software commands, calibrate user-specific gestures and gesture-intentions, and manage the biometric detection device. The user interface can be used to manage the power, gestures, commands, and/or other settings of the biometric detection device.

The authenticating of a user's specific and selected gestures and gesture-intentions may further be comprised of collecting a first set of user biometric data and creating a biometric profile, then collecting a second set of user biometric data and comparing to the first set of biometric data in order to authenticate the user as a function of biometric signal data.

The biometric signals that are detected can be made of eccentric, concentric, or isometric contraction of one or more muscles and/or muscle groups. In some embodiments, these biometric signals are detected through one or more electromyograph electrodes, electrocardiogram electrodes, photodiodes (photoreceptors), ultrasound sensors (e.g., ultrasound transducers), accelerometers, and/or gyroscopes.

The analysis of biometric signal data of the user may be used to create at least one unique key for the user. Such biometric signals may be analyzed through fuzzy logic, pattern classification, computational neural networks, forward dynamic modeling, and/or support vector machines. The unique key or keys may be stored in a memory. The key may be used for security authentication to allow or deny a user access to a device and/or execute customized software programs.

Customized software commands, as descried herein, provide binding and/or linking a function, as implemented by a processor of a biometric and identification control system, to one or more gestures (e.g., also described herein as user-specific and user-selected gesture-intentions) of a user that is to be executed by the processor upon a user initiating those one or more gestures. The customized software function may also include a security authentication to lock or unlock an object, to initiate a third party mechanically automated process, hardware component, and or initiate a software program.

In some embodiments, a user voluntary gesture (i.e., a user-specific and user-selected gesture-intention) can be defined by, or selected from, a list of predetermined gestures. Additionally, or alternatively, a user voluntary gesture (i.e., a user-specific and user-selected gesture-intention) can be a unique voluntary gesture that is defined by or simply performed by the user.

In various embodiments, a biometric detection and identification control system can be any combination of a wearable, implantable, and/or a remote device. The components for the detection of biometric signals can be in contact with the user, subcutaneously positioned to the user, implanted within the user, or within proximity to the user.

The biometric identification and control system may comprise an adaptive learning component that is configured to identify user-specific and user-selected gesture-intention(s) based on collected or detected biosignals. These biosignals may be analyzed using a pattern recognition component that allows the addition or removal of biometric feedback data to optimize the adaptive learning component.

In some embodiments, digital recording of a biometric profile can defines a first and second user-specific and user-selected gesture-intention of the user. In such embodiments, the second user-specific and user-selected gesture-intention may be recorded in a sequence with the user-specific and user-selected gesture-intention of the user. The sequence may then be bound to a security interface and may be required to provide authentication of the user for access to the secure resource or device.

In various embodiments, a user-specific and user-selected gesture-intention corresponds to a user-specific and user-selected gesture-intention of the user where an actuated voluntary gesture is a resulting physical response of the user initiated upon performance of the user-specific and user-selected gesture-intention.

In some embodiments, a biometric profile may further comprises a second electronic recording of a second biosignal representation of the user. The second biosignal representation may either be deliberately not bound to the security interface or filtered by the processor to prevent access to the security interface.

In accordance with the above, and with the disclosure herein, the present disclosure includes improvements in computer functionality or in improvements to other technologies at least because the present disclosure recites that, e.g., a computing device, such as a wearable computing device, is enhanced via the biometric software or other components herein that allow for enhanced security and/or authentication of the computing or wearable device itself or via interfacing with other computing devices to provide or implement increased security via biometric signals. That is, the present disclosure describes improvements in the functioning of the computer itself or "any other technology or technical field" because a computing device, such as wearable, can be updated or enhanced to provide authentication and/or access to secure resource(s) and/or device(s), which can include real-world objects such as doors and lock screens and the like. This improves over the prior art at least because the systems and methods herein provide for a faster and/or more secure way of accessing such secure resource(s) and/or device(s).

The present disclosure relates to improvement to other technologies or technical fields at least because the present disclosure relates to the field of security and authentication, wherein, in the present invention allows a wearable device to unlock or otherwise provide access to real-world objects, including physical objects (e.g., mechanical locks and door) and/or computing resources (e.g., computers and laptops via replacing traditional password login with a biometric login using a user's user-specific and user-selected gesture-intention).

In addition, the present disclosure includes applying certain aspects or features, as described herein, with, or by use of, a particular machine, e.g., a wearable device or other similar device to provide authentication of the user for access to a secure resource or device.

The present disclosure includes effecting a transformation or reduction of a particular article to a different state or thing, e.g., transformation or reduction of biometric signals of a user to authentication and security output used to provide authentication of the user for access to a secure resource or device The present disclosure includes specific features other than what is well-understood, routine, conventional activity in the field, or adding unconventional steps that confine the claim to a particular useful application, e.g., biometric identification and control systems and methods for providing customizable security through authentication of biosignal representations of one or more user-specific and user-selected gesture-intentions Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein.

Figure 1A:
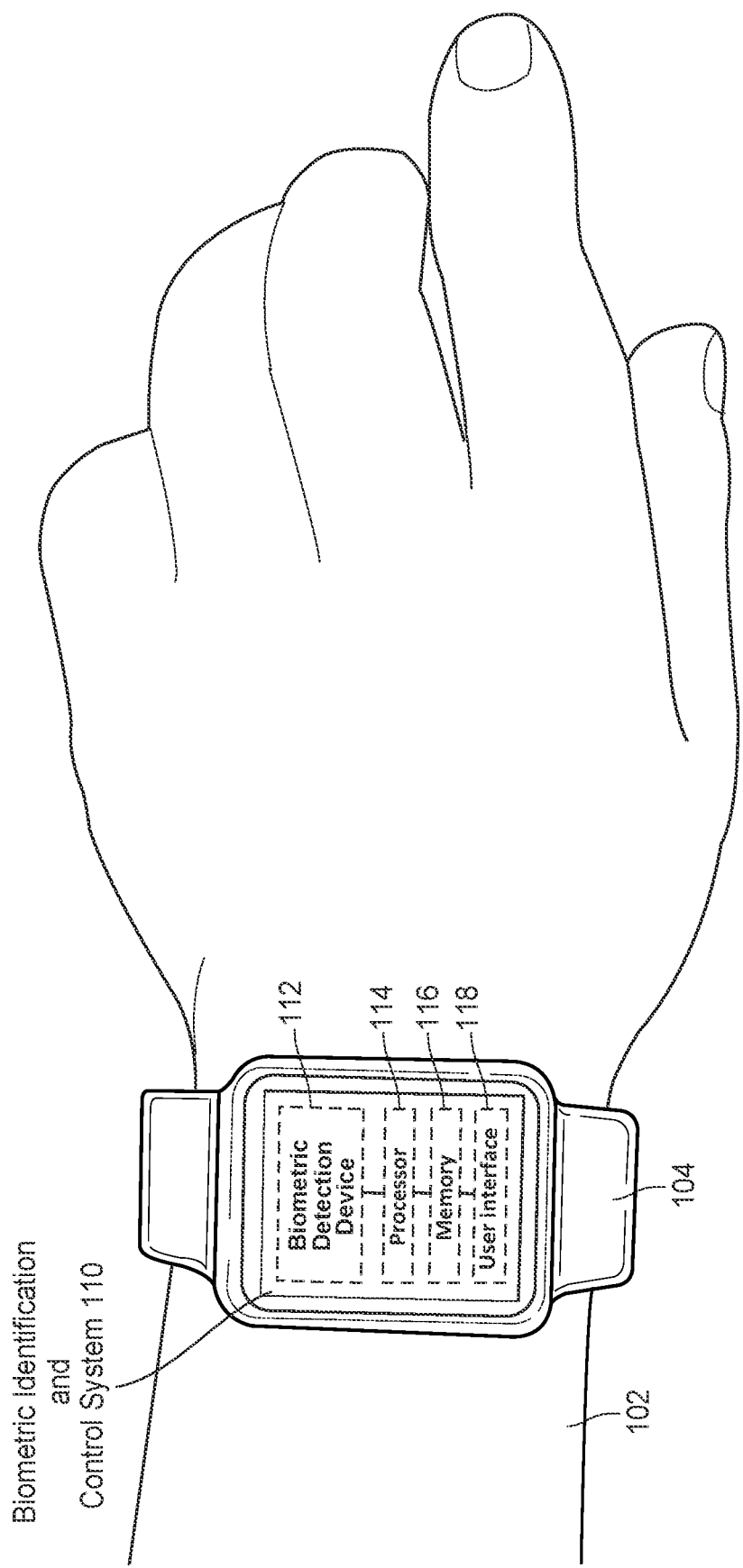
FIG. 1A illustrates a block diagram of an example biometric identification and control system in accordance with various embodiments herein.

The Figures depict preferred embodiments for purposes of illustration only. Alternative embodiments of the systems and methods illustrated herein may be employed without departing from the principles of the invention described herein.

DETAILED DESCRIPTION

While the present invention is susceptible of embodiment in many different forms, there are shown in the drawings and will be described herein in detail specific exemplary embodiments thereof, with the understanding that the present disclosure is to be considered as an exemplification of the principles of the invention and is not intended to limit the invention to the specific embodiments illustrated. In this respect, before explaining at least one embodiment consistent with the present invention in detail, it is to be understood that the invention is not limited in its application to the details of construction and to the arrangements of components set forth above and below, illustrated in the drawings, or as described in the examples. Methods and apparatuses consistent with the present invention are capable of other embodiments and of being practiced and carried out in various ways. Also, it is to be understood that the phraseology and terminology employed herein, as well as the abstract included below, are for the purposes of description and should not be regarded as limiting.

FIG. 1A illustrates a block diagram of an example biometric identification and control system 110 in accordance with various embodiments herein. Biometric identification and control system 110 is configured to provide customizable security through authentication of biosignal representations of one or more user-specific and user-selected gesture-intentions.

As illustrated by FIG. 1A, biometric identification and control system 110 comprises a biometric detection device 112 configured to detect biometric signals and/or data of a user 102. In various embodiments, biometric detection device 112 may comprise at least one of (a) one or more electromyographic electrodes; (b) one or more electrocardiogram electrodes; (c) one or more photodiodes; (d) one or more ultrasound transducers; (e) one or more accelerometers; (f) one or more gyroscopes; (g) one or more infrared sensors; or (h) one or more ultrasound sensors. Additionally, or alternatively, biometric detection device 112 may at least be one of an implantable device (e.g., implanted on or within a user's body and/or skin); a wearable device (e.g., such as a watch, arm band, leg band, etc.); or a remote detection device (e.g., such as a remote control or other device cable of sensing biometric signals of a user). Additionally, or alternatively, biometric detection device 112 may be configured to be at least one of: subcutaneous positioned with respect to the user, in contact with the user, implanted within the user, and/or within a proximity to the user.

The biometric identification and control system 110 further comprises a processor 114 communicatively coupled to biometric detection device 112. Processor 114 may comprise a microprocessor, system on a chip (SoC), or processor, such as an ARM, ATOM, INTEL, or other similar processor (e.g., as typically used with wearable or similar devices) for executing computing instructions, applications, source code, or otherwise software (e.g., of software component) as depicted or described herein.

The biometric identification and control system 110 further comprises a biometric software component comprising computing instructions executable by processor 114. The software component may be stored on a memory 116 communicatively coupled (e.g., via a SoC or computing bus) to processor 114.

Execution of the computing instructions of the software component by processor 114 causes processor 114 to perform an analysis of the biometric signal data of the user as detected by biometric detection device 112. For example, software component (e.g., stored in memory 116) may contain computing instructions executable by processor 114. The computing instructions may be software implemented in a programming language such as Java, C, C++, C #, Ruby, etc., and compiled to execute on processor 114 or may be otherwise be configured to be interpreted or run by processor 114.

Figure 1B:
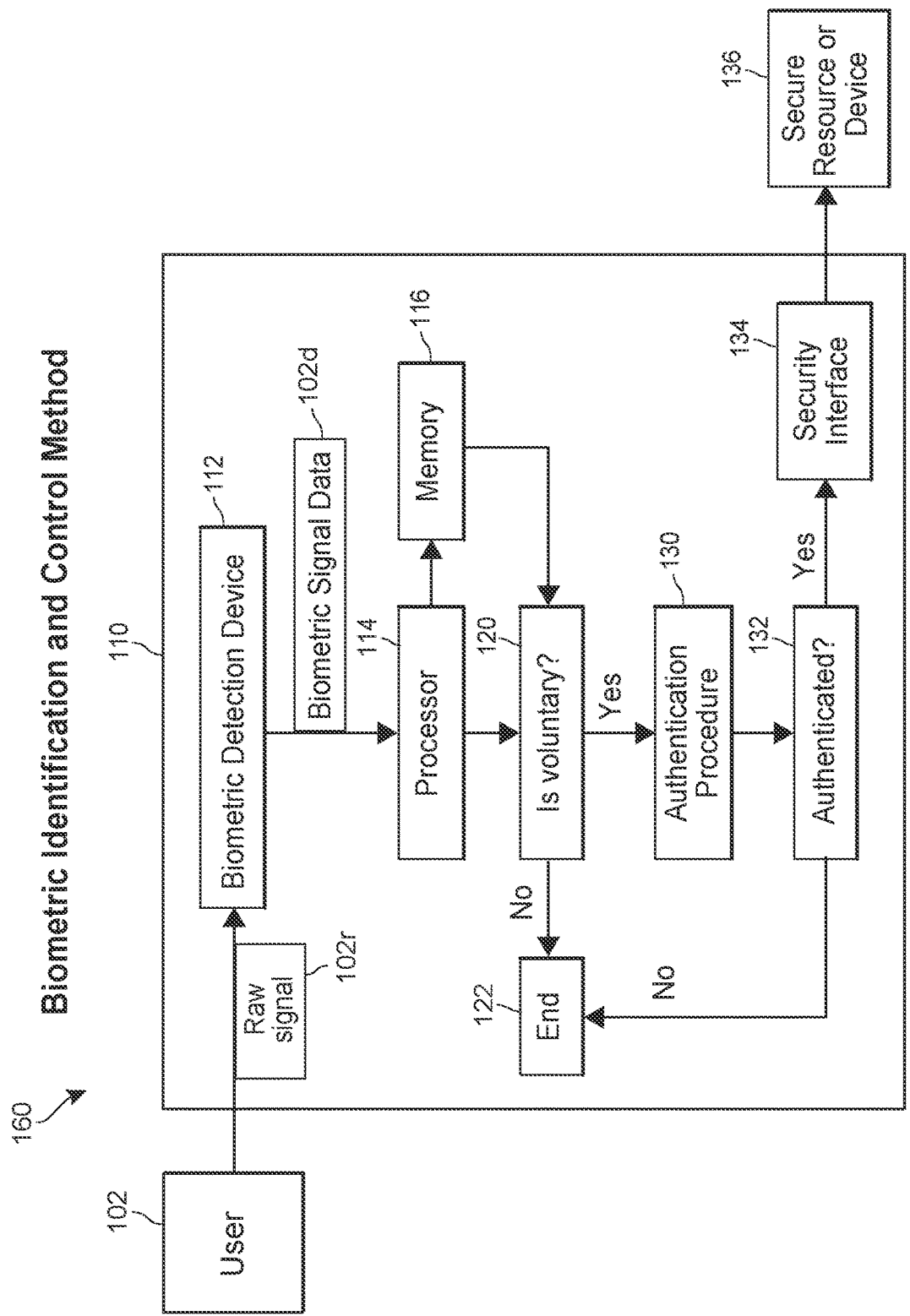
FIG. 1B illustrates a flow diagram of an example biometric identification and control method in accordance with various embodiments herein.
Figure 2A:
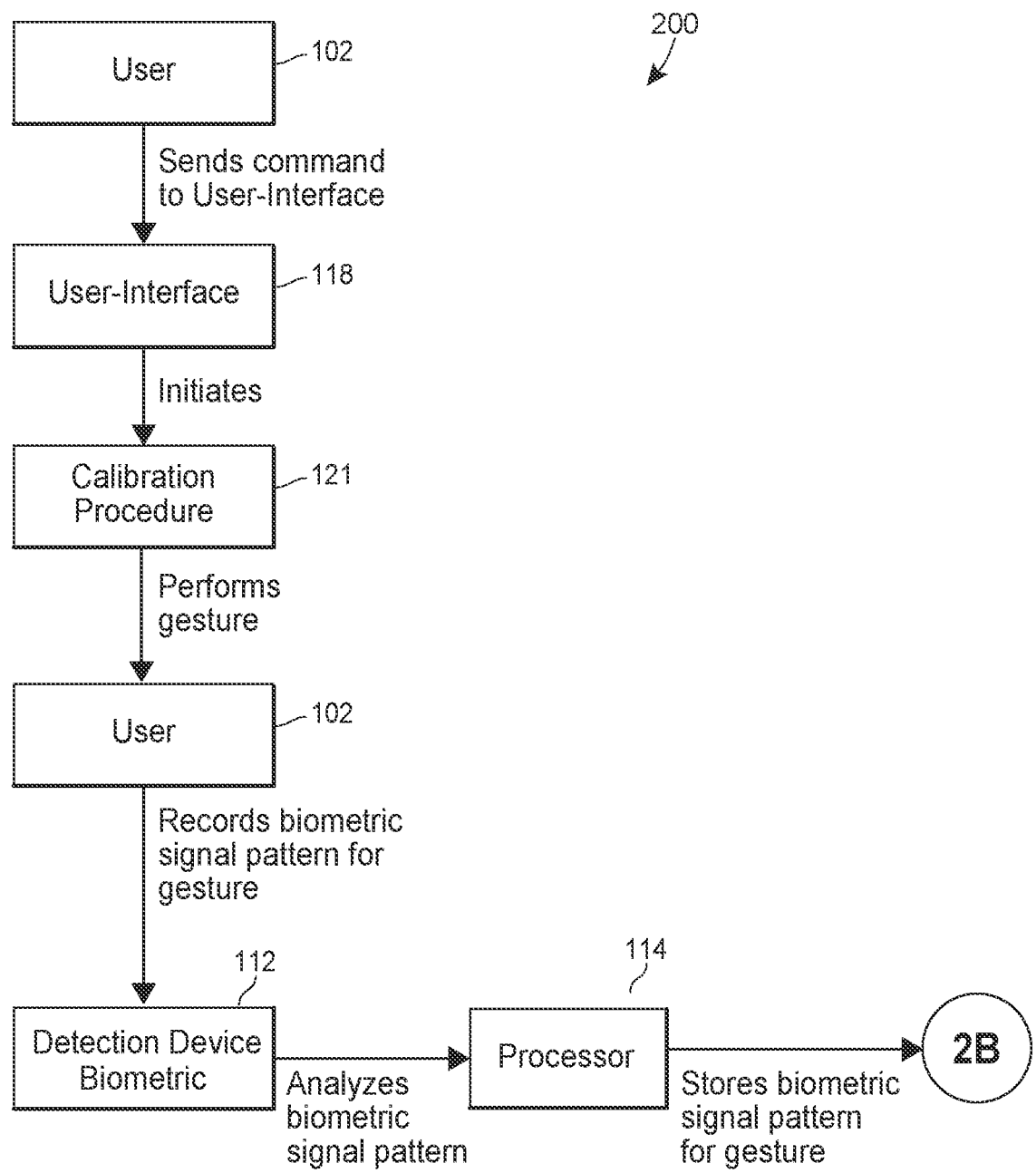
FIG. 2A illustrates a first portion of a flow diagram of an example gesture recording and authentication procedure as initiated by user-specific and user-selected gesture-intentions and in accordance with various embodiments herein.

In various embodiments, computing instructions of the software component (e.g., stored in memory 116) may comprise a "while" loop executing to perform one or more portions of algorithms, methods, and/or flow diagrams as described and/or illustrated for FIGS. 1B, 2A, and/or 2B or otherwise described herein. For example, the "while loop" may execute or operate (e.g., via execution of processor 114) to detect and/or record biometric signal data of user 102 as detected and/or received by biometric detection device 112. In such embodiments, detection and/or receipt of the biometric signal data would result in a "true" condition or state that would trigger the while loop to execute the one or more portions or blocks of FIGS. 1B, 2A, and/or 2B or otherwise described herein.

Additionally, or alternatively, computing instructions of the software component (e.g., stored in memory 116) may comprise one or more event listeners, such as a listener function programmed to detect and/or receive biometric signal data of user 102 as detected and/or received by biometric detection device 112. In this way, biometric signals (e.g., electromyographic (EMG)) of user 102 would be pushed to, or otherwise received by, biometric detection device 112 to detect or generate the biometric signal data and trigger the listener function that would then be used by the one or more portions or blocks of FIGS. 1B, 2A, and/or 2B or otherwise described herein.

Figure 4:
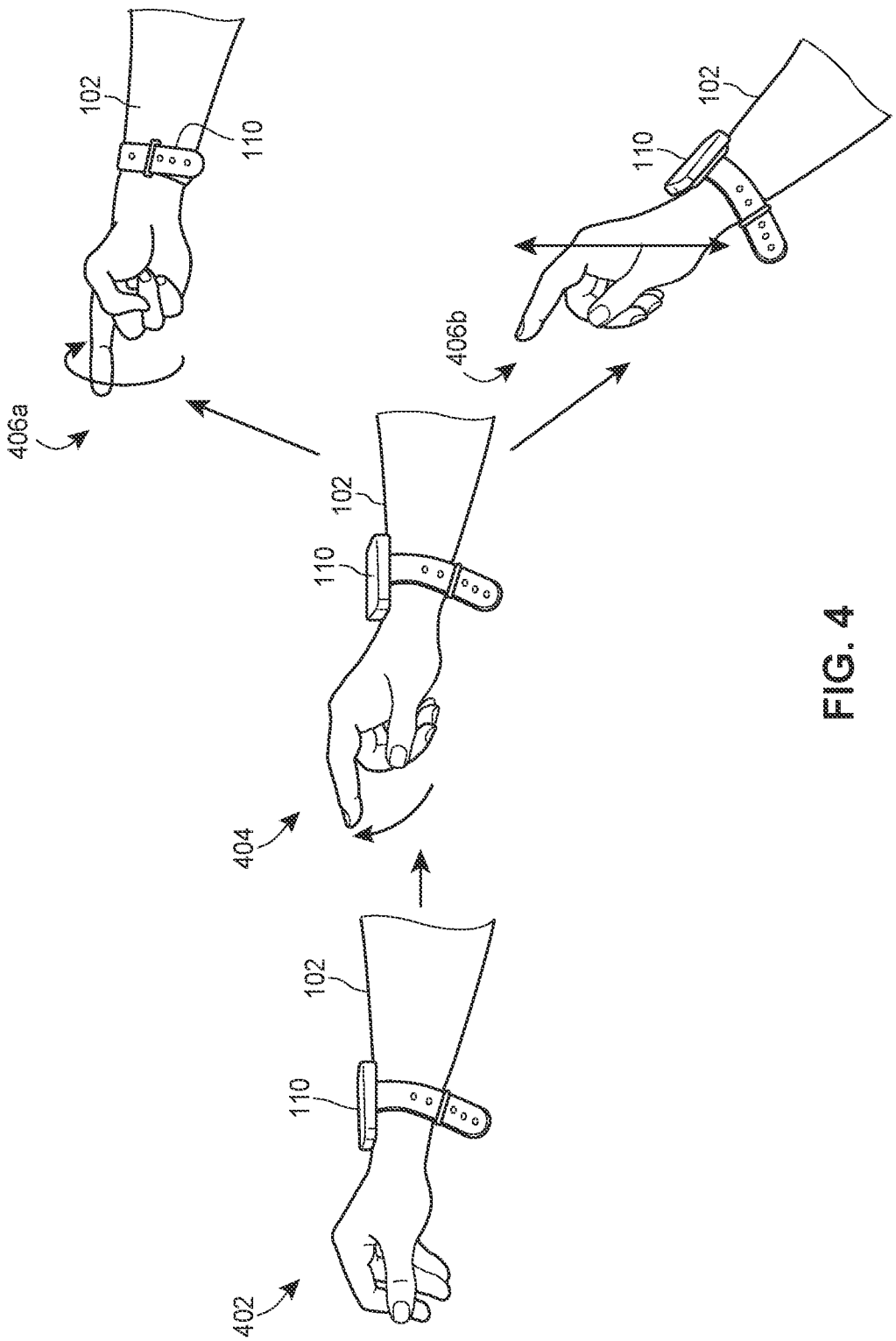
FIG. 4 illustrates example user-specific and user-selected gesture-intentions of a user.

In some embodiments biometric software component comprises an adaptive learning component configured to identify or detect user-specific and user-selected gesture-intention(s) (e.g., user-specific and user-selected gesture-intentions 402, 404, 406a, and/or 406b as described and illustrated by FIG. 4 herein) as performed by the user (e.g., user 102) and causing the generation of biometric signal data (e.g., biometric signal data 102d) as detected for the user.

Additionally, or alternatively, biometric software component may further be configured to use or modify biometric signal (e.g., user 102) data to train or optimize the adaptive learning component for identification or detection of the user-specific and user-selected gesture-intention.

As described herein, the adaptive learning component may be trained using a supervised or unsupervised machine learning program or algorithm. The machine learning program or algorithm may employ a neural network, which may be a convolutional neural network, a deep learning neural network, or a combined learning module or program that learns in two or more features or feature datasets in a particular areas of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques. Machine learning may involve identifying and recognizing patterns in existing data (such as user-specific and user-selected gesture-intentions as identified in patterns of biometric signal data, e.g., biometric signal data 102d) in order to facilitate making predictions for subsequent data (to identify or detect further user-specific and user-selected gesture-intentions as made by the user for the purpose of providing authentication of the user for access to a secure resource or device as described herein).

Machine learning model(s), such as those of adaptive learning component, may be created and trained based upon example (e.g., "training data,") inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based on the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

For example, in FIG. 1B, adaptive learning component may be loaded in memory 116 and may be trained with biometric signal data 102d to recognize user-specific and user-selected gesture-intentions (e.g., user-specific and user-selected gesture-intentions 402, 404, 406a, and/or 406b). The adaptive learning component may then receive further or new biometric signal data 102d, where biometric signals of user 102 may be detected as a given user-specific and user-selected gesture-intentions (e.g., user-specific and user-selected gesture-intentions 402, 404, 406a, and/or 406b), which may then be used to provide authentication of the user for access to a secure resource or device as described herein.

Referring to FIG. 1B, execution of the computing instructions by processor 114 causes processor 114 to create a biometric profile based on the analysis of the biometric signal data. In various embodiments, the biometric profile comprises an electronic recording of a biosignal representation of a user-specific and user-selected gesture-intention of the user as described herein.

In addition, execution of the computing instructions by processor 114 causes processor 114 to bind the user-specific and user-selected gesture-intention of the user to a security interface as described and illustrated herein, e.g., for FIGS. 1A, 1B, 2A, and/or 2B or otherwise herein. The security interface is operable to provide authentication of the user for access to a secure resource or device as described and/or illustrated herein, e.g., for FIGS. 1B, 2A, and/or 2B or otherwise herein In some embodiments, the biometric software component (e.g., stored in memory 116) may comprises a user interface (e.g., a user interface 118) configured to receive one or more selections of the user for customizing the security interface for operation in accordance with the user-specific and user-selected gesture-intention. The user interface may comprise various kinds or types. For example, in some embodiments, the user interface may comprise a button user interface, such as a depressible and/or toggle button, that when pressed causes biometric identification and control system 110 to operate in different modes and/or states (e.g., learning mode, gesture mode, etc.). For example, the learning mode may be toggled or selected when the user trains biometric identification and control system 110 to detect, record, and/or recognize one or more user-specific and user-selected gesture-intentions of user 102 as described herein. Gesture mode may be toggled or selected when the user is ready to use or implement biometric identification and control system 110 to detect and/or recognize one or more user-specific and user-selected gesture-intentions of user 102 as described herein.

Additionally, or alternatively, a user interface may comprise a virtual user interface configured to display at least a portion of the biometric profile. Such virtual user interface may comprise a graphic user interface (GUI). Additionally, or alternatively, a virtual user interface may comprise (a) a customized software command editing function, (b) a gesture calibration function, and/or (c) a biometric detection apparatus manager. For example, the customized software command editing function may be rendered via a GUI or screen of the biometric identification and control system 110 (e.g., on a wearable device such as a watch, arm band, etc.). The customized software command editing function may allow a user (e.g., user 102) to edit parameters and/or configurations of the biometric identification and control system 110 to control how and what actions that biometric identification and control system 110 performs or takes when detecting biometric signal data. This may include editing the types and/or number or gestures. It may also allow a user to a user to configure biometric identification and control system 110 to operate and/or interface with various security interface(s) and/or secure resource(s) and/or device(s) as described herein.

As an additional example, the gesture calibration function may be rendered via a GUI or screen of the biometric identification and control system 110 (e.g., on a wearable device such as a watch, arm band, etc.). The gesture calibration function may allow a user (e.g., user 102) to train, set up, or otherwise configure biometric identification and control system 110 to detect and/or recognize one or more user-specific and user-selected gesture-intentions of user 102 as described herein.

As a still further example, the biometric detection apparatus manager may be rendered via a GUI or screen of the biometric identification and control system 110 (e.g., on a wearable device such as a watch, arm band, etc.). The biometric detection apparatus manager may allow a user (e.g., user 102) to adjust the sensitivity of biometric detection device 112 to control the detection sensitivity (e.g., the degree of when a signal is detected) and/or filtering of biometric signal data as received by user 102.

As illustrated for FIG. 1A, each of biometric detection device 112, processor 114, memory 116, and/or user interface 118 may be communicatively coupled to one other via a computer, SoC interface, and/or other electronic interface.

In additional embodiments, biometric detection device 112, processor 114, memory 116, and/or user interface 118 may be part of separate computing devices, which are communicatively coupled, e.g., via a wired or wireless connection. For example, in one embodiment, user interface 114 may be implemented on a separate or remote computing device (e.g., a laptop or computer) in wireless communication (e.g., BLUETOOTH or WIFI (802.11)) with biometric identification and control system 110, where a user configures the biometric identification and control system 110 (e.g., by training or otherwise configuring the biometric software component as described herein) via the remote user interface 114 on the separate computing device. The biometric detection apparatus manager, or other software components, etc., may also be implemented or configured on separate computing device in communication with biometric identification and control system 110.

FIG. 1B illustrates a flow diagram of an example biometric identification and control method 160 in accordance with various embodiments herein. Biometric identification and control method 160 illustrates customizable security through authentication of biosignal representations of one or more user-specific and user-selected gesture-intentions. In some embodiments, a tangible, non-transitory computer-readable medium may store instructions (e.g., in memory 116) for providing customizable security through authentication of biosignal representations of one or more user-specific and user-selected gesture-intentions. The instructions, when executed by one or more processors, cause the one or more processors to execute the blocks or steps as described for FIG. 1B.

With reference to FIG. 1B, biometric identification and control method 160 comprises performing, by a biometric software component executing on processor 114 communicatively coupled to biometric detection device 112, an analysis of biometric signal data of a user (e.g., user 102 of FIG. 1A) as detected by biometric detection device 112. In various components, software component may be stored in memory 116 and/or otherwise configured or set up as described for FIG. 1A or elsewhere herein. In various embodiments, biometric detection device 112 may receive raw signal data 102r of user 102 and generate, transform, pass through, identify, and/or otherwise detect biometric signal data 102d for analyzing by processor 114. Biometric detection device 112 may detect raw signal data 102r and/or biometric signal data 102d of user 102 as described herein for FIG. 1A.

In various embodiments biometric signal data 102d may be analyzed with at least one of the following algorithms or computational techniques, including: (a) fuzzy logic; (b) pattern classification; (c) computational neural networks; (d) forward dynamic modelling; or (e) support vector machines. In various embodiments, such data analysis may comprise creating at least one user-specific authentication key as described herein. The user-specific authentication key is unique to a user-specific and user-selected gesture-intention of a user (e.g., user 102).

With reference FIG. 1B, biometric identification and control method 160 further comprises creating, by the biometric software component, a biometric profile based on the analysis of the biometric signal data. In various embodiments the biometric profile may be stored in memory 116.

Figure 3:
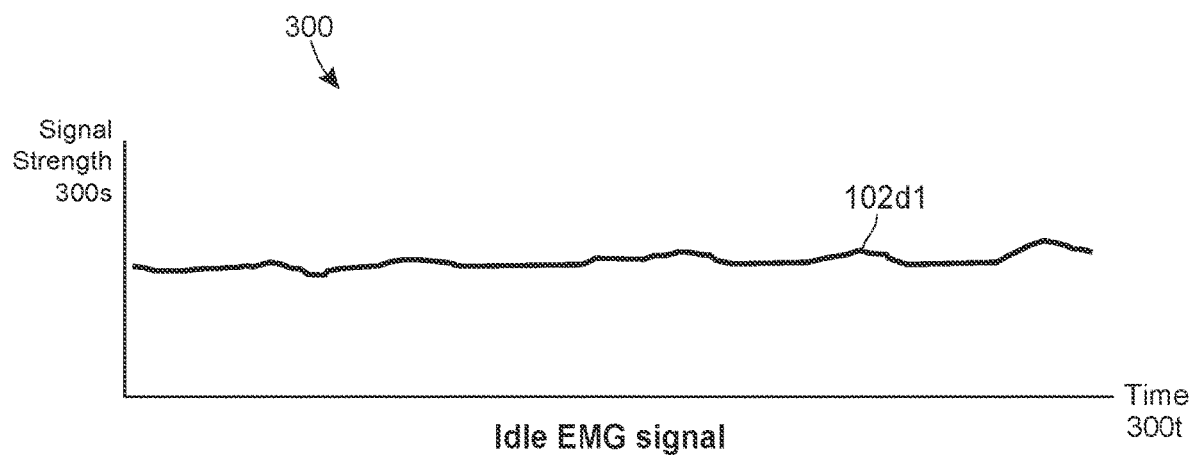
FIG. 3 illustrates examples of biometric signal data of a user.
Figure 3:
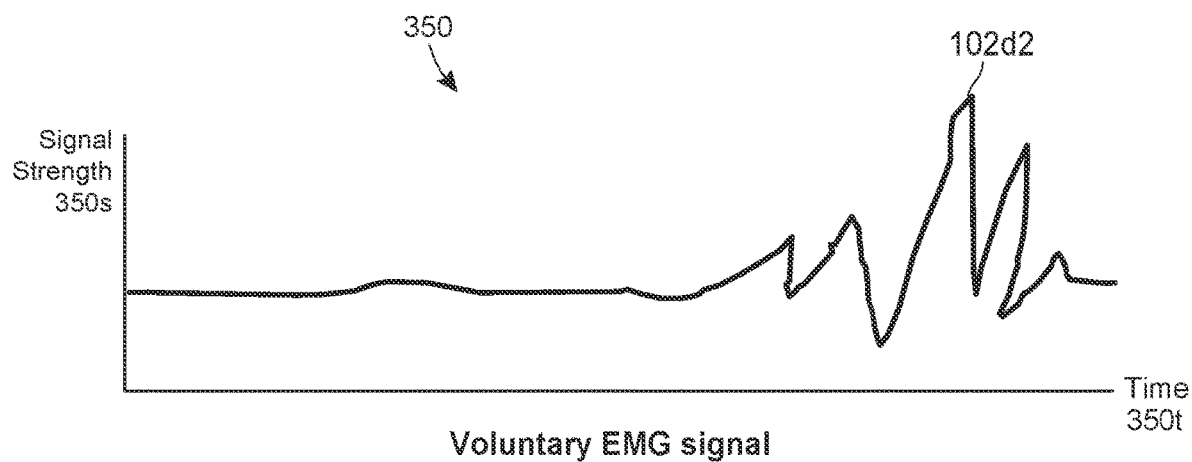

In various embodiments, the biometric profile may comprise an electronic recording of a biosignal representation of a user-specific and user-selected gesture-intention of the user. Biometric profile may comprise an electronic recording (e.g., as illustrated by FIG. 3) of a biosignal representation of a user-specific and user-selected gesture-intention of the user. For example, the biosignal representation of a user-specific and user-selected gesture-intention of the user may be defined by the biometric signal data 102 as detected for the user (e.g., user 102).

FIG. 3 illustrates examples of biometric signal data (e.g., idle biometric signal data 102d1 and voluntary biometric signal data 102d2) of a user (e.g., user 102). Such biometric signal data may be used to define or otherwise represent a user-specific and user-selected gesture-intention of the user. For example, the biometric signal data illustrated by FIG. 3 may comprise biometric signal data 102 as detected for the user (e.g., user 102) as illustrated and/or described for FIGS. 1A and/or 1B or elsewhere herein. In various embodiments, a user-specific and user-selected gesture-intention, or biometric signals or data thereof, may comprise at least one of: eccentric contraction of one or more muscles or muscle groups of a user (e.g., user 102); concentric contraction of one or more muscles or muscle groups of a user (e.g., user 102); and/or isometric contraction of one or more muscles or muscle groups of the user (e.g., user 102). Such activity (e.g., anyone one or more types of contraction of a muscle and/or muscle groups) may cause electromyographic (EMG) signals to be produced by user 102 that may be detected by biometric detection device 112 as described herein.

For example, FIG. 3, illustrates a comparative representation of biometric signal data 102d (e.g., which is illustrated as EMG data—idle biometric signal data 102d1 and voluntary biometric signal data 102d2—as received by biometric detection device 112). In the example of FIG. 3, diagram 300 illustrates biometric signal data 102d1 as received (over time 300t), recorded, identified or as otherwise detected when a user (e.g., user 102) is at rest, i.e., is not performing a gesture or gesture intention, such as a user-specific and user-selected gesture-intention as a described herein. Biometric signal data 102*d*1 is detected over time 300*t* at various signal strength 300*s*, which as a whole, indicates a data pattern that defines a user-specific and user-selected gesture-intention (or lack thereof as shown for the embodiment of diagram 300). Such biometric signal data (e.g., biometric signal data 102*d*1) may be detected by biometric detection device 112 as described herein.

Conversely, in the example of FIG. 3, diagram 350 illustrates biometric signal data 102*d*2 as received (over time 350*t*), recorded, identified or as otherwise detected when a user (e.g., user 102) is active, e.g., is performing a gesture or gesture intention, such as a user-specific and user-selected gesture-intention as a described herein. Biometric signal data 102*d*2 is detected over time 350*t* at various signal strength 350*s*, which as a whole, indicates a data pattern that defines or represents a user-specific and user-selected gesture-intention (as shown for the embodiment of diagram 350). The data pattern, varying across time 350*t* at different signal strengths, as shown for diagram 350 of FIG. 3, uniquely defines the user-specific and user-selected gesture-intention for the user (e.g., user 102). Such biometric signal data (e.g., biometric signal data 102*d*2) may be detected by biometric detection device 112 as described herein. In various embodiments, such data pattern may be used to generate, record, create, provide, or otherwise implement a given user-specific and user-selected gesture-intention as described herein. In some embodiments, such detection of biometric signal data may cause a user-specific authentication key to be provided to allow for security authentication as provided herein.

FIG. 4 illustrates example user-specific and user-selected gesture-intentions (e.g., user-specific and user-selected gesture-intentions 402, 404, 406*a*, and 406*b*) of a user (e.g., user 102). The user-specific and user-selected gesture-intentions (e.g., user-specific and user-selected gesture-intentions 402, 404, 406*a*, and 406*b*) of FIG. 4 illustrate several examples of voluntary gestures (e.g., a series of user-specific and user-selected gesture-intentions) that may be performed or implemented by user 102 to generate the biometric signal data (e.g., biometric signal data 102*d*2 as described for FIG. 3). The various gestures, together and/or alone, generate or produce different biometric patterns (e.g., biometric signal data 102*d*2) that result in unique data signal that can be detected (e.g., by biometric detection device 112) and that can be used to bind, drive, or otherwise setup commands, actions, or security interfaces, such as authentication commands, actions, and/or security interfaces to provide to access secure resources or devices as described herein.

In the example of FIG. 4, a series of user-specific and user-selected gesture-intentions, with alternatives or additions (e.g., gestures 406*a* and 406*b*) is illustrated. For example, such series begins with user-specific and user-selected gesture-intention 402 in which user 102 performs a pinch gesture with his or her hands and/or fingers. The pinch gesture performed by the user causes biometric signals (e.g., generated by contraction of user 102's muscles or muscle groups as described herein, such as muscles of the user's hand, finger, wrist, forearm, and/or other muscles) to be received and/or detected by biometric detection device 112 of biometric identification and control system 110, which in the example of FIG. 4 is illustrated as implemented via a wearable device (e.g., a watch based device).

Next, the series illustrated by FIG. 4 further comprises user-specific and user-selected gesture-intention 404 in which user 102 performs a point gesture with his or her hand and/or fingers. The point gesture performed by the user causes biometric signals (e.g., generated by contraction of user 102's muscles or muscle groups as described herein, such as muscles of the user's hand, finger, wrist, forearm, and/or other muscles) to be received and/or detected by biometric detection device 112 of biometric identification and control system 110 (e.g., a watch based device as shown in FIG. 4). The biometric signals generated for the point gesture may be, and typically are, different from those generated and detected for the previous pinch gesture.

Still further, the series illustrated by FIG. 4 further comprises user-specific and user-selected gesture-intention 406*a* in which user 102 performs a twirl gesture with his or her hand and/or fingers. The twirl gesture performed by the user causes biometric signals (e.g., generated by contraction of user 102's muscles or muscle groups as described herein, such as muscles of the user's hand, finger, wrist, forearm, and/or other muscles) to be received and/or detected by biometric detection device 112 of biometric identification and control system 110 (e.g., a watch based device as shown in FIG. 4). The biometric signals generated for the twirl gesture may be, and typically are, different from those generated and detected for the previous pinch and/or point gesture(s).

Additionally, or alternatively, the series illustrated by FIG. 4 further comprises user-specific and user-selected gesture-intention 406*b* in which user 102 performs a lift gesture with his or her hand and/or fingers. The lift gesture performed by the user causes biometric signals (e.g., generated by contraction of user 102's muscles or muscle groups as described herein, such as muscles of the user's hand, finger, wrist, forearm, and/or other muscles) to be received and/or detected by biometric detection device 112 of biometric identification and control system 110 (e.g., a watch based device as shown in FIG. 4). The biometric signals generated for the lift gesture may be, and typically are, different from those generated and detected for the previous pinch, point, and/or twirl gesture(s).

Any one or more of the user-specific and user-selected gesture-intentions (e.g., any one or more of user-specific and user-selected gesture-intentions 402, 404, 406*a*, and/or 406*b*) may comprise a user-specific and user-selected gesture-intention, either singularly or as a whole, for binding to a security interface and/or to provide authentication of the user for access to a secure resource or device as described herein. That is, in some embodiments only a single user-specific and user-selected gesture-intention may be implemented to comprise a given user-specific and user-selected gesture-intention for security access purposes as described herein. In other embodiments, a sequence of user-specific and user-selected gesture-intentions may be implemented to comprise a given user-specific and user-selected gesture-intention for security access purposes as described herein. For example, where a sequence is implemented, the electronic recording of the biometric profile may further define a second user-specific and user-selected gesture-intention of the user. The second user-specific and user-selected gesture-intention may be recorded in a sequence with a first user-specific and user-selected gesture-intention of the user. Such a sequence may be bound to the security interface (e.g., security interface 134). In various embodiments, the sequence may be required or implemented to provide authentication of the user for access to a secure resource or device (e.g., secure resource or device 136) as described herein.

For example, with reference to FIG. 4, in some embodiments, the lift gesture of user-specific and user-selected gesture-intention 406*b* may be used separately from the twirl gesture of user-specific and user-selected gesture-intention 406a, in which only user-specific and user-selected gesture-intentions 402, 404, and 406a together, as a whole or in a sequence, comprise a comprehensive user-specific and user-selected gesture-intention used to bind to a security interface and/or to provide authentication of a user for access to a secure resource or device as described herein. In other embodiments, the lift gesture of user-specific and user-selected gesture-intention 406b may be part of (and may follow) the twirl gesture of user-specific and user-selected gesture-intention 406a, in which all user-specific and user-selected gesture-intentions 402, 404, 406a, and 406b together, as a whole and in a sequence, comprise a comprehensive user-specific and user-selected gesture-intention used to bind to a security interface and/or to provide authentication of a user for access to a secure resource or device as described herein.

It is to be understood that the gestures as illustrated by FIG. 4 are merely a subset of examples and that any one or more gestures, movements, or actions performed by the user (e.g., user 102) that generate biometric signals (e.g., EMG signals) may be used to generate biometrical signal data for use by the biometric identification and control systems and method described herein. In addition, it is to be understood that one gesture or a series of gestures (e.g., as illustrated for Example 4) may be used to define a user-specific and user-selected gesture-intention as described herein.

In some embodiments, a user-specific and user-selected gesture-intention may be predefined. In such embodiments, a user-specific and user-selected gesture-intention (e.g., any of user-specific and user-selected gesture-intentions 402, 404, 406a, and/or 406b as described for FIG. 4) may be defined by a list of one or more predetermined gestures as provided to the user to select from. For example, such a list may be displayed via user interface 118 of biometric identification and control system 110. The list may also be displayed on another user interface (such as a graphic user interface (GUI)) of a computing device having a processor and communication interface (e.g., a laptop, computer, etc. communicatively coupled via a BLUETOOTH or WIFI interface) to biometric identification and control system 110.

Additionally, or alternatively, a user-specific and user-selected gesture-intention (e.g., any of user-specific and user-selected gesture-intentions 402, 404, 406a, and/or 406b as described for FIG. 4) may be defined by one or more unique gestures or gesture intentions as defined by the user. For example, FIG. 4 illustrates, at least in some embodiments, one or more of user-selected gesture-intentions 402, 404, 406a, and/or 406b that may be unique gestures or gesture intentions as defined by or otherwise chosen by user 102.

In some embodiments, a user-specific and user-selected gesture-intention may comprise an actuated gesture that is a resulting physical response of the user initiated upon performance of the user-specific and user-selected gesture-intention. For example, such actuated gesture may include a reflex of user 102, such as a natural reflex, brought on by a previous gesture such that the actuated gesture is the natural or learned next gesture that flows or follows a previous gesture. This can include a pinch gesture followed by a pinch out or pinch in gesture. Another example includes a thumb-up gesture followed by a relaxing of the thumb gesture. Still further, another example may include a point gesture followed by a retracting gesture, where user 102 points his or her finger in a first gesture and where the actuated gesture is a retracting gesture where the finger returns to a state of rest following the point gesture.

In some embodiments, certain user gestures may be filtered or otherwise ignored. This allows biometric identification and control system 110 to streamline or otherwise filter biometric signal data 102d, which can improve or better the efficiency of analysis by processor 114 by removing unwanted or unused biometric signal data. In some embodiments, user gestures as represented by a user's biosignal representation may be stored in a user's biometric profile for filtering or otherwise ignoring. For example, in some embodiments, a biometric profile of a user (e.g., user 102) may further comprise a second electronic recording of a second biosignal representation of a second user-specific and user-selected gesture-intention of the user. The second electronic recording and its corresponding second user-specific and user-selected gesture-intention of the user may be second to a primary or first electronic recording and its corresponding primary or first user-specific and user-selected gesture-intention of the user used to bind to a security interface and/or to provide authentication of a user for access to a secure resource or device as described herein. In such embodiments, in order to filter or otherwise ignore the second user-specific and user-selected gesture-intention, the second user-specific and user-selected gesture-intention may be at least one of: (1) deliberately not bound to the security interface (as described herein), or (2) filtered by processor 114 to prevent access to the secure resource or device as described herein.

In some embodiments, a biometric profile, as described herein, further may comprise a user-specific authentication key. A user-specific authentication key may comprise or be based on a digital representation of biometric data of a user, such as biometric signal data 102, including, for example, 102d1 and/or voluntary biometric signal data 102d2, and/or combinations thereof, as shown and described herein for FIG. 3 or otherwise herein. In other embodiments, user-specific authentication key may be a cryptographic key generated based on the biometric data of a user, such as biometric signal data 102, including, for example, 102d1 and/or voluntary biometric signal data 102d2, and/or combinations thereof.

In some embodiments, the biometric signal data may be used as a seed value (e.g., a random seed value) to generate or create the user-specific authentication key as a cryptographic key. In such embodiments, the user-specific authentication key may be generated with the biometric signal data using an encryption algorithm, such as an RSA security algorithm, MD5 encryption algorithm, HMAC encryption algorithm, or the like.

In various embodiments, the user-specific authentication key may be generated and/or provided when a user (e.g., user 102) performs a user-specific and user-selected gesture-intention as described herein. For example, a user-specific authentication key may be generated when a user trains or updates biometric detection device 112 to learn a new user-specific and user-selected gesture-intention. Additionally, or alternatively, a user-specific authentication key, as already trained, may be provided (e.g., from biometric profile and/or memory 116) when a user performs an existing user-specific and user-selected gesture-intention. In various embodiments, the user-specific authentication key may authorize the user to access to the secure resource or device as described herein.

As shown in the embodiment of FIG. 1B, biometric identification and control method 160 comprises processor 114 that analyzes biometric signal data 102d to detect user-specific and user-selected gesture-intention(s) as described herein. In some embodiments, the detected user-specific and user-selected gesture-intention(s) may be stored in memory 116 (e.g., such as stored in or as part of a biometric profile of a user (user 102) as described herein). In other embodiments, processor 114 may access memory 114 to load or otherwise access a prerecorded or existing user-specific and user-selected gesture-intention for authentication of a user for access to a secure resource or device as described herein.

At block 120, processor 114 may determine whether a biometric signal data 102d matches or is otherwise is representative of a known, trained, recorded, or existing user-specific and user-selected gesture-intention. For example, the software component may comprise a pattern recognition component to detect patterns among biometric signals and thereby detect user-specific and user-selected gesture-intention(s) (e.g., user-specific and user-selected gesture-intentions 402, 404, 406a, and/or 406b). Such determination may include recognition of a voluntary biometric signal data pattern, e.g., such as voluntary biometric signal data 102d2. If no such voluntary biometric data pattern is recognized or detected, then biometric identification and control method 160 may end (at block 122) for a given iteration, where an iteration comprises receipt of one or more biometric signals, e.g., biometric signal data 102d.

If a voluntary biometric data pattern is recognized or detected at block 120, and matched with an existing or recorded user-specific and user-selected gesture-intention, then biometric identification and control method 160 continues to block 130 for the given iteration, An iteration comprises receipt of one or more biometric signals, e.g., biometric signal data 102d, at biometric detection device 112. At block 130, an authentication procedure that may be performed by processor 114. In various embodiment, the authentication procedure (at block 130) may comprise determining whether a user-specific and user-selected gesture-intention matches, is similar to, or is otherwise representative of a known, trained, recorded, or existing user-specific and user-selected gesture-intention. Once matched or identified, the specific and user-selected gesture-intention may provide authentication for the user (e.g., user 102). For example, in various embodiments, authentication of a user-specific and user-selected gesture-intention may comprise: (a) collecting a first set of user biometric data (e.g., biometric signal data 102d) of the user during a first iteration, and creating a biometric profile (e.g., as stored in memory 116) corresponding to the user-specific and user-selected gesture-intention; (b) collecting a second set of biometric data (e.g., biometric signal data 102d) of the user during a second iteration; and (c) authenticating (at block 130) that the biometric signals of the second set of user biometric data has a similarity with (or otherwise matches or is representative of) the first set of biometric data of the biometric profile. Similarity may be determined based on a provided threshold or tolerance, where the threshold or tolerance is a numerical value that defines a difference in signal strength overtime time (e.g., as illustrated for FIG. 3, e.g., voluntary biometric signal data 102d2) that the second set of biometric data may differ from the first set of biometric data in order for an identification, match, detection, or otherwise recognition of the user-specific and user-selected gesture-intention to occur. Such threshold or tolerance may be defined in terms of signal strength such as voltage, amperes (amps), or other signal values of numerical type or quantity.

At block 132, processor 114 determines whether a given user-specific and user-selected gesture-intention (e.g., as performed by user 102) is authenticated. If a given user-specific and user-selected gesture-intention is not authenticated, then biometric identification and control method 160 may end (at block 122) for a given iteration, where an iteration comprises receipt of one or more biometric signals, e.g., biometric signal data 102d.

If a given user-specific and user-selected gesture-intention is authenticated, then biometric identification and control method 160 continues for a given iteration, where an iteration comprises receipt of one or more biometric signals, e.g., biometric signal data 102d.

With reference to FIG. 1B, biometric identification and control method 160 further comprises binding, by the biometric software component, a user-specific and user-selected gesture-intention of the user to a security interface 134. Security interface 134 is operable to provide authentication of the user (e.g., user 102) for access to a secure resource or device (e.g., a locked device, such as a physical lock or a virtual lock implemented as part of a physical and/or virtual security unit, system, platform, etc. such as described for FIG. 5 herein).

For example, in various embodiments, user-specific and user-selected gesture-intention(s) (e.g., user-specific and user-selected gesture-intentions 402, 404, 406a, and/or 406b) of a user (e.g., user 102)) may each, together or alone, and/or in various combinations, be bound to security interface 134. Once bound to security interface 134, a user may implement any of the one or more user-specific and user-selected gesture-intention(s) (e.g., user-specific and user-selected gesture-intentions 402, 404, 406a, and/or 406b) to access or otherwise interact with a secure resource or device 136.

In some embodiments, biometric identification and control method 160 may comprise linking a function of secure resource or device 136 to one or more user-specific and user-selected gesture-intention(s) (e.g., user-specific and user-selected gesture-intentions 402, 404, 406a, and/or 406b) thereby binding such one or more user-specific and user-selected gesture-intention(s) to security interface 134 and secure resource or device 136. In such embodiments, the linking function is configured to execute upon the user initiating the user-specific and user-selected gesture-intention.

In various embodiments herein, security interface 134 comprises an application programming interface (API) that may include source code and/or hardware for communicating or otherwise interacting with (e.g., via wired or wireless communication) secure resource or device 136. In some embodiments, secure resource or device 136 may have a separate API or interface as provided by a manufacturer or provider (e.g., third party) of secure resource or device 136. In such embodiments, security interface 134 may interface or interact with (e.g., via BLUETOOTH, WIFI, USB connection, or otherwise) secure resource or device 136 to access secure resource or device 136.

In some embodiments, by way of non-limiting example, a secure resource or device 136 may comprise a physical lock (e.g., a lock of door, such as a building or home door, or door of a vehicle, or other such asset) wherein a function that is linked comprises locking or unlocking the physical lock. The function may be linked or bound to a user-specific and user-selected gesture-intention (e.g., user-specific and user-selected gesture-intentions 402, 404, 406a, and/or 406b) via security interface 134 as described herein.

In additional embodiments, for example, a secure resource or device 136 may comprise a mechanically automated process (e.g., opening of a garage door via interaction with a garage door opener) wherein the function that is linked comprises controlling or accessing the mechanically automated process. The function may be linked or bound to a user-specific and user-selected gesture-intention (e.g., user-specific and user-selected gesture-intentions 402, 404, 406a, and/or 406b) via security interface 134 as described herein.

In still further embodiments, for example, a secure resource or device 136 may comprise a hardware component (e.g., a lock box that has an API for receiving a wireless unlock signal) and wherein the function comprises controlling or accessing the hardware component. The function may be linked or bound to a user-specific and user-selected gesture-intention (e.g., user-specific and user-selected gesture-intentions 402, 404, 406a, and/or 406b) via security interface 134 as described herein.

In still further embodiments, for example, a secure resource or device 136 may comprise a software program having a lock screen or secure data and wherein the function comprises initiating or accessing the software program. The function may be linked or bound to a user-specific and user-selected gesture-intention (e.g., user-specific and user-selected gesture-intentions 402, 404, 406a, and/or 406b) via security interface 134 as described herein.

Figure 5:
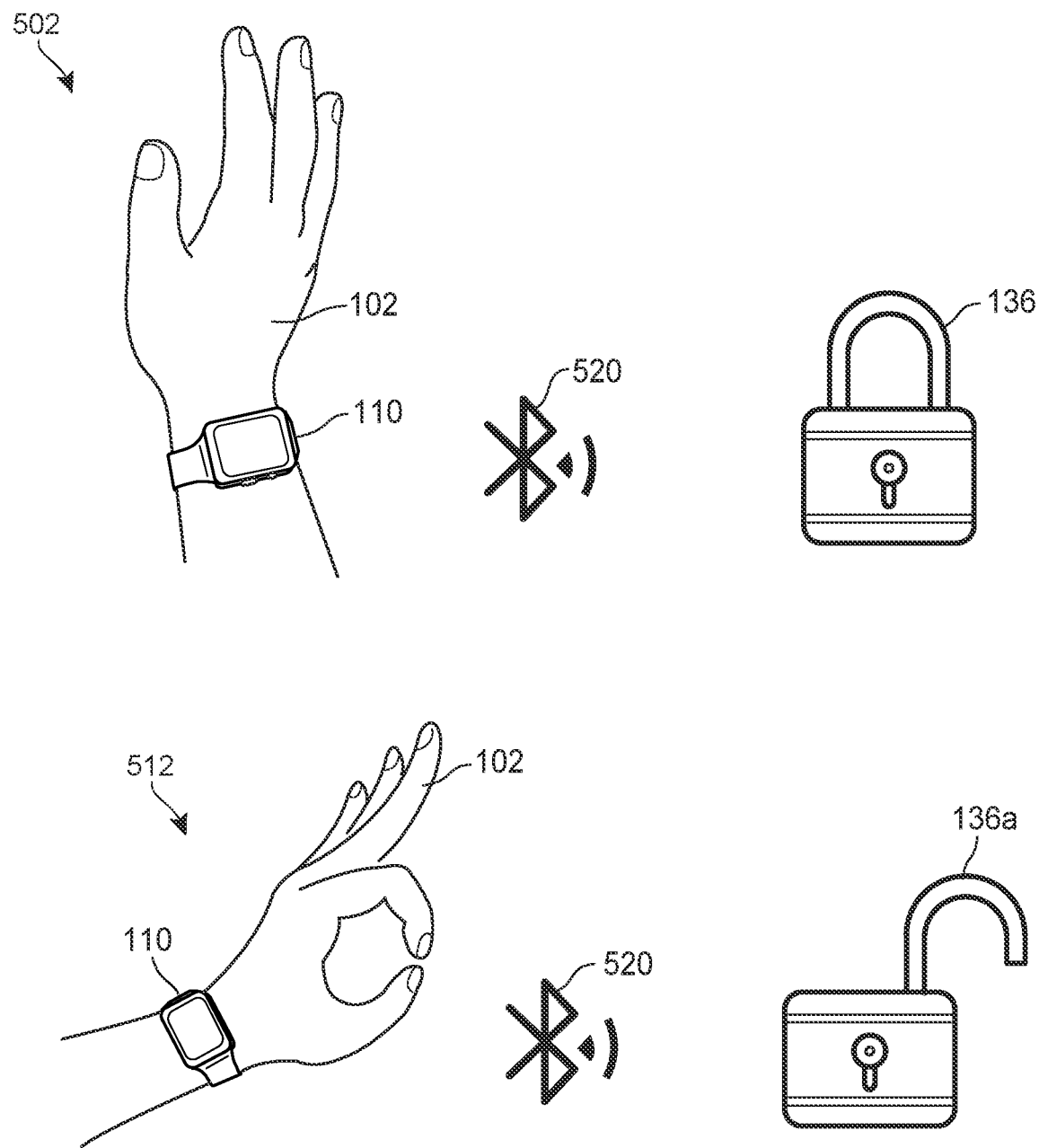
FIG. 5 illustrates an example secure resource or device and a user-specific and user-selected gesture-intention performed to access the secure resource or device.

FIG. 5 illustrates an example secure resource or device 136 (e.g., a physical lock or representation of a virtual lock of a computing resource or device) and a user-specific and user-selected gesture-intention (okay gesture 512) performed to access the secure resource or device 136. User hand 502 illustrates a user's hand (e.g., of user 102) at rest. Biometric signals of the user (e.g., user 102) are received or detected by biometric detection device 112 of biometric identification and control system 110, whereby biometric signal data 102d is determined and analyzed as described herein. Biometric signal data 102d1 of FIG. 3 is representative of biometric data generated by user hand 502. Biometric identification and control system 110 is depicted in FIG. 5 as a wearable device (e.g., a watch or arm band). In addition, biometric identification and control system of FIG. 10 is communicatively coupled to secure resource or device 136 via a wireless connection 520 (e.g., BLUETOOTH or WIFI (802.11 standard)). Through wireless connection 520, the biometric signals can be transmitted to secure resource or device 136 (e.g., a physical lock or representation of a virtual lock of a computing resource or device) via security interface 134 as described herein.

As shown for FIG. 5, user hand 512 illustrates the user's hand (e.g., of user 102) during an okay gesture 512. Biometric signals of the user (e.g., user 102), during okay gesture 512, are received or detected by biometric detection device 112 of biometric identification and control system 110, whereby biometric signal data 102d is determined and analyzed as described herein. Biometric signal data 102d2 of FIG. 3 is representative of biometric data generated by user hand 512. Through wireless connection 520, the biometric signals, as generated by the user's okay gesture 512, are transmitted to secure resource or device 136 (e.g., a physical lock or representation of a virtual lock of a computing resource or device) via security interface 134 as described herein. In the embodiment of FIG. 5, the okay gesture 512 unlocks secure resource or device 136 to place secure resource or device 136 in unlocked state 136a. Accordingly, in the embodiment of FIG. 5, biometric identification and control system 110 has previously been trained or otherwise configured (e.g., by recording and storing okay gesture 512) to recognize or detect a given user-specific and user-selected gesture-intention (okay gesture 512) and that gesture is bound to security interface 134 for unlocking secure resource or device 136 (e.g., the physical lock or representation of a virtual lock of a computing resource or device).

In various embodiments, secure resource or device 136 may be a device provided by a third party company, such as a lock of door that locked or unlocked via security interface 134. In such embodiments, performance of the given user-specific and user-selected gesture-intention (okay gesture 512) may unlock the door and provide access to a room, house, building, area, vehicle, or other physical object or asset. In other embodiments, secure resource or device 136 may be a virtual lock, such as a lock screen on a mobile device or computer screen, whereby performance of the given user-specific and user-selected gesture-intention (okay gesture 512) may unlock and provide access to software, screens, or other virtual or computing resources on a computing device, GUI, or other software resources or assets.

FIG. 2A illustrates a first portion 200 of a flow diagram of an example gesture recording and authentication procedure as initiated by user-specific and user-selected gesture-intentions and in accordance with various embodiments herein. FIG. 2A illustrates a first iteration of biometric identification and control system 110 receiving a first set of biometric signal data 102d. As shown for FIG. 2A, user 102 sends a command to user-interface 118 to initiate a calibration procedure 121. User-interface 118 may be a button interface or a virtual interface as described herein. Calibration procedure then prompts or otherwise allows a user 102 to perform a user-specific and user-selected gesture-intention (e.g., any of user-specific and user-selected gesture-intentions 402, 404, 406a, and/or 406b as described and illustrated by FIG. 4 herein) for recording. Biometric detection device 112 receives and detects the user's biometric signal data 102d of user 102, which is recorded, and analyzed by processor 114. Memory 116 may then store the biometric signal pattern for the related user-specific and user-selected gesture-intention. The stored or otherwise recorded user-specific and user-selected gesture-intention may then be implemented or used as described in FIG. 2B.

Figure 2B:
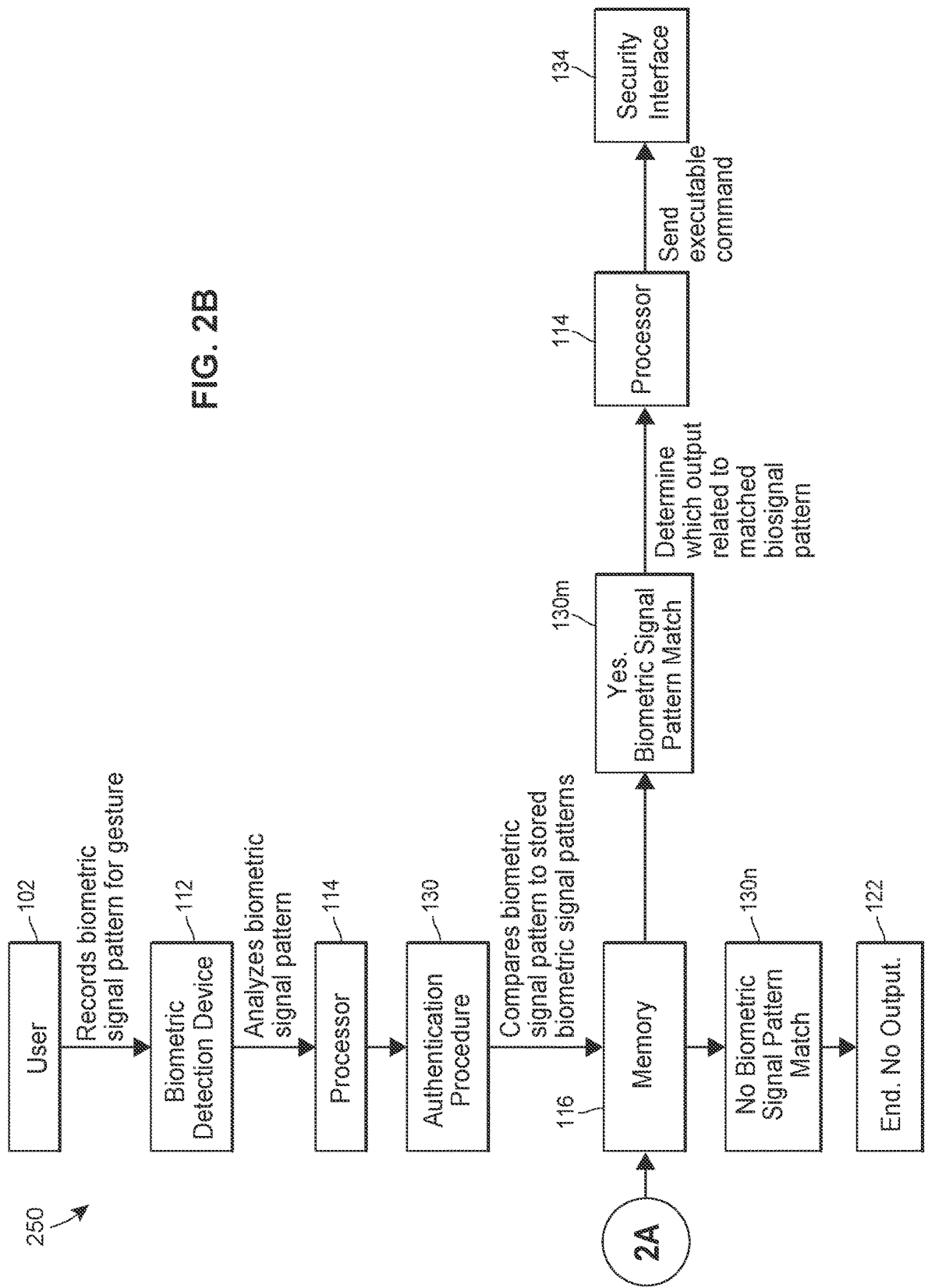
FIG. 2B illustrates a second portion of the flow diagram of FIG. 2A illustrating the example gesture recording and authentication procedure as initiated by user-specific and user-selected gesture-intentions and in accordance with various embodiments herein.

FIG. 2B illustrates a second portion 250 of the flow diagram of FIG. 2A illustrating the example gesture recording and authentication procedure as initiated by user-specific and user-selected gesture-intentions and in accordance with various embodiments herein. FIG. 2B illustrates a second iteration of biometric identification and control system 110 receiving a second set of biometric signal data 102d. As shown for FIG. 2B, biometric detection device 112 receives and detects the user's biometric signal data 102d of user 102, which may be recorded, and analyzed by processor 114. Biometric identification and control system 110 may then implement authentication procedure 130 as described herein. In some embodiments, as shown for FIG. 2B, processor 114 may access memory 116 to compare biometric signal data 102d to existing (stored) data patterns or signals of one or more user-specific and user-selected gesture-intention(s) (e.g., any of user-specific and user-selected gesture-intentions 402, 404, 406a, and/or 406b as described and illustrated by FIG. 4 herein). If there is no biometric signal pattern match (130n), then security interface 134 is not invoked or otherwise accessed, and the current iteration, for the currently received biometric signal data 102d, ends (122). However, if there is a biometric signal pattern match (130m), then security interface 134 is invoked or otherwise accessed, and, for the current iteration, i.e., for the currently received biometric signal data 102d, the security interface 134 provides authentication of the user for access to a secure resource or device (e.g., secure resource or device 136) as described herein.

Aspects of the Present Disclosure

The following aspects of the disclosure are exemplary only and not intended to limit the scope of the disclosure.

1. A biometric identification and control system configured to provide customizable security through authentication of biosignal representations of one or more user-specific and user-selected gesture-intentions, the biometric identification and control system comprising: a biometric detection device configured to detect biometric signal data of a user; a processor communicatively coupled to the biometric detection device; and a biometric software component comprising computing instructions executable by the processor, wherein execution of the computing instructions by the processor causes the processor to: perform an analysis of the biometric signal data of the user as detected by the biometric detection device, create a biometric profile based on the analysis of the biometric signal data, the biometric profile comprising an electronic recording of a biosignal representation of a user-specific and user-selected gesture-intention of the user, and bind the user-specific and user-selected gesture-intention of the user to a security interface, wherein the security interface is operable to provide authentication of the user for access to a secure resource or device.

2. The biometric and identification control system of aspect 1, wherein the biometric software component comprises a user interface configured to receive one or more selections of the user for customizing the security interface for operation in accordance with the user-specific and user-selected gesture-intention.

3. The biometric and identification control system of aspect 2, wherein the user interface comprises at least one of: (1) a button user interface, or (2) a virtual user interface configured to display at least a portion of the biometric profile, wherein the biometric profile further comprises at least one of: (a) a customized software command editing function, (b) a gesture calibration function, or (c) a biometric detection apparatus manager.

4. The biometric and identification control system of any one of aspects 1-3, wherein the authentication of the user-specific and user-selected gesture-intention comprises: (a) collecting a first set of user biometric data of the user, and creating a biometric profile corresponding to the user-specific and user-selected gesture-intention; (b) collecting a second set of biometric data of the user; and (c) authenticating that the biometric signals of the second set of user biometric data has a similarity with the first set of biometric data of the biometric profile.

5. The biometric and identification control system of any one of aspects 1-4, wherein the user-specific and user-selected gesture-intention comprises at least one of: eccentric contraction of one or more muscles or muscle groups of the user; concentric contraction of one or more muscles or muscle groups of the user; or isometric contraction of one or more muscles or muscle groups of the user.

6. The biometric and identification control system of any one of aspects 1-5, wherein the biometric detection device comprises at least one of (a) one or more electromyographic electrodes; (b) one or more electrocardiogram electrodes; (c) one or more photodiodes; (d) one or more ultrasound transducers; (e) one or more accelerometers; (f) one or more gyroscopes; (g) one or more infrared sensors; or (h) one or more ultrasound sensors.

7. The biometric and identification control system of any one of aspects 1-6, wherein the analysis of the biometric signal data of the user comprises data analysis of the biometric signal data with at least one of: (a) fuzzy logic; (b) pattern classification; (c) computational neural networks; (d) forward dynamic modelling; or (e) support vector machines, and wherein the data analysis comprises creating at least one user-specific authentication key that is unique to the user-specific and user-selected gesture-intention of the user.

8. The biometric and identification control system of aspect 7, wherein the biometric profile further comprises the user-specific authentication key.

9. The biometric and identification control system of aspect 7, wherein the user-specific authentication key is generated or provided when the user performs the user-specific and user-selected gesture-intention, and wherein the user-specific authentication key authorizes the user to access to the secure resource or device.

10. The biometric and identification control system of any one of aspects 1-9 further comprising linking a function of the secure resource or device to the user-specific and user-selected gesture-intention, wherein the function is configured to execute upon the user initiating the user-specific and user-selected gesture-intention.

11. The biometric and identification control system of aspect 10, wherein the secure resource or device comprises at least one of: a physical lock wherein the function that is linked comprises locking or unlocking the physical lock; a mechanically automated process wherein the function that is linked comprises controlling or accessing the mechanically automated process; a hardware component and wherein the function comprises controlling or accessing the hardware component; or a software program and wherein the function comprises initiating or accessing the software program.

12. The biometric and identification control system of any one of aspects 1-11, wherein the user-specific and user-selected gesture-intention is defined by at least one of: (1) a list of one or more predetermined gestures as provided to the user to select from; or (2) one or more unique gestures or gesture intentions as defined by the user.

13. The biometric and identification control system of any one of aspects 1-12, wherein the biometric detection device comprises at least one of: an implantable device, a wearable device, or a remote detection device.

14. The biometric and identification control system of any one of aspects 1-13, wherein the biometric software component comprises an adaptive learning component configured to identify the user-specific and user-selected gesture-intention performed by the user based on the biometric signal data as detected for the user.

15. The biometric and identification control system of any one of aspect 1-14, wherein the biometric software component comprises a pattern recognition component.

16. The biometric and identification control system of aspect 14, wherein the biometric software component is further configured to modify the biometric signal data to optimize the adaptive learning component for identification of the user-specific and user-selected gesture-intention.

17. The biometric identification and control system of any one of aspects 1-16, wherein the electronic recording of the biometric profile further defines a second user-specific and user-selected gesture-intention of the user, wherein the second user-specific and user-selected gesture-intention is recorded in a sequence with the user-specific and user-selected gesture-intention of the user, and wherein the sequence is bound to the security interface, and wherein the sequence is required to provide authentication of the user for access to the secure resource or device.

18. The biometric identification and control system of any one of aspects 1-17, wherein the user-specific and user-selected gesture-intention comprises an actuated gesture that is a resulting physical response of the user initiated upon performance of the user-specific and user-selected gesture-intention.

19. The biometric identification and control system of any one of aspects 1-18, wherein the biometric detection device is further configured to be at least one of: subcutaneous positioned with respect to the user, in contact with the user, implanted within the user, or within a proximity to the user.

20. The biometric identification and control system of any one of aspects 1-19, wherein the biometric profile further comprises a second electronic recording of a second biosignal representation of a second user-specific and user-selected gesture-intention of the user, wherein the second user-specific and user-selected gesture-intention is at least one of: (1) deliberately not bound to the security interface, or (2) filtered by the processor to prevent access to the secure resource or device.

21. A biometric identification and control method for providing customizable security through authentication of biosignal representations of one or more user-specific and user-selected gesture-intentions, the biometric identification and control method comprising: performing, by a biometric software component executed by a processor communicatively coupled to a biometric detection device, an analysis of biometric signal data of a user as detected by the biometric detection device; creating, by the biometric software component, a biometric profile based on the analysis of the biometric signal data, the biometric profile comprising an electronic recording of a biosignal representation of a user-specific and user-selected gesture-intention of the user; and binding, by the biometric software component, the user-specific and user-selected gesture-intention of the user to a security interface, wherein the security interface is operable to provide authentication of the user for access to a secure resource or device.

22. A tangible, non-transitory computer-readable medium storing instructions for providing customizable security through authentication of biosignal representations of one or more user-specific and user-selected gesture-intentions, that when executed by one or more processors cause the one or more processors to: perform, by a biometric software component executed by a processor communicatively coupled to a biometric detection device, an analysis of biometric signal data of a user as detected by the biometric detection device; create, by the biometric software component, a biometric profile based on the analysis of the biometric signal data, the biometric profile comprising an electronic recording of a biosignal representation of a user-specific and user-selected gesture-intention of the user; and bind, by the biometric software component, the user-specific and user-selected gesture-intention of the user to a security interface, wherein the security interface is operable to provide authentication of the user for access to a secure resource or device.

Additional Considerations

Although the disclosure herein sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed is:

1. A biometric identification and control system configured to provide customizable security through authentication of biosignal representations of one or more user-specific and user-selected gesture-intentions, the biometric identification and control system comprising:
    a biometric detection device configured to detect biometric signal data of a user, wherein the biometric detection device is configured to detect the biometric signal data as one or more of: eccentric contractions of one or more muscles or muscle groups of the user, and concentric contractions of one or more muscles or muscle groups of the user, and isometric contractions of one or more muscles or muscle groups of the user;
    a processor communicatively coupled to the biometric detection device; and
    a biometric software component comprising computing instructions executable by the processor, wherein execution of the computing instructions by the processor causes the processor to:
    perform an analysis of the biometric signal data produced by muscle tissue of the user and as detected by the biometric detection device,
    create a biometric profile based on the analysis of the biometric signal data, the biometric profile comprising an electronic recording of a biosignal representation of a user-specific and user-selected gesture-intention of the user, and
    bind the user-specific and user-selected gesture-intention of the user to a security interface, wherein the security interface is operable to provide authentication of the user for access to a secure resource or device.

2. The biometric and identification control system of claim 1, wherein the biometric software component comprises a user interface configured to receive one or more selections of the user for customizing the security interface for operation in accordance with the user-specific and user-selected gesture-intention.

3. The biometric and identification control system of claim 2, wherein the user interface comprises at least one of: (1) a button user interface, or (2) a virtual user interface configured to display at least a portion of the biometric profile,
    wherein the biometric profile further comprises at least one of: (a) a customized software command editing function, (b) a gesture calibration function, or (c) a biometric detection apparatus manager.

4. The biometric and identification control system of claim 1, wherein the authentication of the user-specific and user-selected gesture-intention comprises: (a) collecting a first set of user biometric data of the user, and creating a biometric profile corresponding to the user-specific and user-selected gesture-intention; (b) collecting a second set of biometric data of the user; and (c) authenticating that the biometric signals of the second set of user biometric data has a similarity with the first set of biometric data of the biometric profile.

5. The biometric and identification control system of claim 1, wherein the user-specific and user-selected gesture-intention comprises at least one of: eccentric contraction of one or more muscles or muscle groups of the user; concentric contraction of one or more muscles or muscle groups of the user; or isometric contraction of one or more muscles or muscle groups of the user.

6. The biometric and identification control system of claim 1, wherein the biometric detection device comprises at least one of (a) one or more electromyographic electrodes; (b) one or more electrocardiogram electrodes; (c) one or more photodiodes; (d) one or more ultrasound transducers;

(e) one or more accelerometers; (f) one or more gyroscopes; (g) one or more infrared sensors; or (h) one or more ultrasound sensors.

7. The biometric and identification control system of claim 1, wherein the analysis of the biometric signal data of the user comprises data analysis of the biometric signal data with at least one of: (a) fuzzy logic; (b) pattern classification; (c) computational neural networks; (d) forward dynamic modelling; or (e) support vector machines, and wherein the data analysis comprises creating at least one user-specific authentication key that is unique to the user-specific and user-selected gesture-intention of the user.

8. The biometric and identification control system of claim 7, wherein the biometric profile further comprises the user-specific authentication key.

9. The biometric and identification control system of claim 7, wherein the user-specific authentication key is generated or provided when the user performs the user-specific and user-selected gesture-intention, and wherein the user-specific authentication key authorizes the user to access to the secure resource or device.

10. The biometric and identification control system of claim 1 further comprising linking a function of the secure resource or device to the user-specific and user-selected gesture-intention, wherein the function is configured to execute upon the user-initiating the user-specific and user-selected gesture-intention.

11. The biometric and identification control system of claim 10, wherein the secure resource or device comprises at least one of: a physical lock wherein the function that is linked comprises locking or unlocking the physical lock; a mechanically automated process wherein the function that is linked comprises controlling or accessing the mechanically automated process; a hardware component and wherein the function comprises controlling or accessing the hardware component; or a software program and wherein the function comprises initiating or accessing the software program.

12. The biometric and identification control system of claim 1, wherein the user-specific and user-selected gesture-intention is defined by at least one of: (1) a list of one or more predetermined gestures as provided to the user to select from; or (2) one or more unique gestures or gesture intentions as defined by the user.

13. The biometric and identification control system of claim 1, wherein the biometric detection device comprises at least one of: an implantable device, a wearable device, or a remote detection device.

14. The biometric and identification control system of claim 1, wherein the biometric software component comprises an adaptive learning component configured to identify the user-specific and user-selected gesture-intention performed by the user based on the biometric signal data as detected for the user.

15. The biometric and identification control system of claim 1, wherein the biometric software component comprises a pattern recognition component.

16. The biometric and identification control system of claim 14, wherein the biometric software component is further configured to modify the biometric signal data to optimize the adaptive learning component for identification of the user-specific and user-selected gesture-intention.

17. The biometric identification and control system of claim 1,
wherein the electronic recording of the biometric profile further defines a second user-specific and user-selected gesture-intention of the user,
wherein the second user-specific and user-selected gesture-intention is recorded in a sequence with the user-specific and user-selected gesture-intention of the user, and
wherein the sequence is bound to the security interface, and
wherein the sequence is required to provide authentication of the user for access to the secure resource or device.

18. The biometric identification and control system of claim 1, wherein the user-specific and user-selected gesture-intention comprises an actuated gesture that is a resulting physical response of the user initiated upon performance of the user-specific and user-selected gesture-intention.

19. The biometric identification and control system of claim 1, wherein the biometric detection device is further configured to be at least one of: subcutaneous positioned with respect to the user, in contact with the user, implanted within the user, or within a proximity to the user.

20. The biometric identification and control system of claim 1, wherein the biometric profile further comprises a second electronic recording of a second biosignal representation of a second user-specific and user-selected gesture-intention of the user, wherein the second user-specific and user-selected gesture-intention is at least one of: (1) deliberately not bound to the security interface, or (2) filtered by the processor to prevent access to the secure resource or device.

21. The biometric identification and control system of claim 1, wherein the user-specific and user-selected gesture-intention is predefined in a list of one or more predetermined gestures as provided to the user to select from.

22. The biometric identification and control system of claim 1, wherein the user-specific and user-selected gesture-intention was previously selected by the user from a list of predetermined gesture intentions, and wherein the biometric signal data identifies a series of muscles specific to the user that activate to perform the user-specific and user-selected gesture-intention of the user as selected from the list.

23. A biometric identification and control method for providing customizable security through authentication of biosignal representations of one or more user-specific and user-selected gesture-intentions, the biometric identification and control method comprising:
performing, by a biometric software component executed by a processor communicatively coupled to a biometric detection device, an analysis of biometric signal data of a user as detected by the biometric detection device, wherein the biometric detection device is configured to detect the biometric signal data as one or more of: eccentric contractions of one or more muscles or muscle groups of the user, and concentric contractions of one or more muscles or muscle groups of the user, and isometric contractions of one or more muscles or muscle groups of the user, and wherein the biometric signal data is produced by muscle tissue of the user;
creating, by the biometric software component, a biometric profile based on the analysis of the biometric signal data, the biometric profile comprising an electronic recording of a biosignal representation of a user-specific and user-selected gesture-intention of the user; and
binding, by the biometric software component, the user-specific and user-selected gesture-intention of the user to a security interface, wherein the security interface is operable to provide authentication of the user for access to a secure resource or device.

24. A tangible, non-transitory computer-readable medium storing instructions for providing customizable security through authentication of biosignal representations of one or more user-specific and user-selected gesture-intentions, that when executed by one or more processors cause the one or more processors to:
- perform, by a biometric software component executed by a processor communicatively coupled to a biometric detection device, an analysis of biometric signal data of a user as detected by the biometric detection device, wherein the biometric detection device is configured to detect the biometric signal data as one or more of: eccentric contractions of one or more muscles or muscle groups of the user, and concentric contractions of one or more muscles or muscle groups of the user, and isometric contractions of one or more muscles or muscle groups of the user, and wherein the biometric signal data is produced by muscle tissue of the user;
- create, by the biometric software component, a biometric profile based on the analysis of the biometric signal data, the biometric profile comprising an electronic recording of a biosignal representation of a user-specific and user-selected gesture-intention of the user; and
- bind, by the biometric software component, the user-specific and user-selected gesture-intention of the user to a security interface, wherein the security interface is operable to provide authentication of the user for access to a secure resource or device.

* * * * *

UNITED STATES PATENT AND TRADEMARK OFFICE
CERTIFICATE OF CORRECTION

PATENT NO. : 12,386,936 B2  
APPLICATION NO. : 18/538030  
DATED : August 12, 2025  
INVENTOR(S) : Blair Andrew Lock Page 1 of 1

It is certified that error appears in the above-identified patent and that said Letters Patent is hereby corrected as shown below:

In the Claims

At Column 28, Lines 3-4, "user, and" should be -- user, --.

Signed and Sealed this  
Second Day of December, 2025

John A. Squires  
*Director of the United States Patent and Trademark Office*